United States Patent
Pilgaard et al.

(10) Patent No.: US 8,197,843 B2
(45) Date of Patent: Jun. 12, 2012

(54) DEVICE FOR THE ADMINISTRATION OF AN ACTIVE AGENT TO THE HUMAN SKIN

(75) Inventors: Michael Pilgaard, Copenhagen NV (DK); Jan Marcussen, Taastrup (DK)

(73) Assignee: Coloplast A/S, Humlebaek (DK)

( * ) Notice: Subject to any disclaimer, the term of this patent is extended or adjusted under 35 U.S.C. 154(b) by 1864 days.

(21) Appl. No.: 10/490,278

(22) PCT Filed: Sep. 20, 2002

(86) PCT No.: PCT/DK02/00614
§ 371 (c)(1),
(2), (4) Date: Sep. 23, 2004

(87) PCT Pub. No.: WO03/024431
PCT Pub. Date: Mar. 27, 2003

(65) Prior Publication Data
US 2005/0019383 A1    Jan. 27, 2005

(30) Foreign Application Priority Data
Sep. 21, 2001  (DK) ................................. 2001 01374

(51) Int. Cl.
A61F 13/02   (2006.01)
A61F 13/00   (2006.01)
A61L 15/16   (2006.01)

(52) U.S. Cl. ..................... 424/448; 424/449

(58) Field of Classification Search .................. 604/307; 424/448, 449
See application file for complete search history.

(56) References Cited

U.S. PATENT DOCUMENTS
| 4,367,732 A | 1/1983 | Poulsen et al. |
| 4,573,996 A | 3/1986 | Kwiatek et al. |
| 4,711,781 A | 12/1987 | Nick et al. |

FOREIGN PATENT DOCUMENTS
| CA | 2 319 903 A1 | 4/2001 |
| DE | 32 02 775 A1 | 3/1983 |
| EP | 0 040 862 | 12/1981 |
| GB | 2 100 605 A | 1/1983 |
| GB | 2 180 756 A | 4/1987 |
| GB | 2 184 016 A | 6/1987 |
| WO | WO 89/05619 | 6/1989 |
| WO | WO 94/15562 | 7/1994 |
| WO | WO 95/17866 | 7/1995 |
| WO | WO 9940888 A1 * | 8/1999 |

* cited by examiner

*Primary Examiner* — Isis Ghali
(74) *Attorney, Agent, or Firm* — Coloplast Corp., Coloplast A/S; Daniel G. Chapik; Nicholas R. Baumann

(57) ABSTRACT

An article having an adhesive surface for adhering to human skin that includes a first component constituting a continuous layer and at least a second component which is located in indentations in the adhesive surface of the first component without being in direct contact with the first component. The second component is separated from the first component by a cup shaped barrier layer having a rim which extends into a flange.

21 Claims, 1 Drawing Sheet

DEVICE FOR THE ADMINISTRATION OF AN ACTIVE AGENT TO THE HUMAN SKIN

This is a nationalization of PCT/DK02/00614 filed Sep. 20, 2002 and published in English.

FIELD OF THE INVENTION

The present invention relates to an article having an adhesive surface for adhering to human skin.

BACKGROUND OF THE INVENTION

Patches for dermal and transdermal drug delivery with medically active ingredients as well as wound dressings with active ingredients incorporated are well-known in the art. The active ingredients may be incorporated in a dressing by different means, e.g. being dispersed or soluted in an adhesive or absorbent layer or they may be coated on the skin facing surface of the dressing or patch. When the active ingredient is to be delivered topically, e.g. in the treatment of wounds, corns or warts, the active ingredient may be located as one or more separate zones in the adhesive surface of the dressing.

Problems may arise when the zones comprising active ingredients are placed in direct contact with the other components of the dressing such as the surrounding adhesive or absorbent component. The other components of the dressing may migrate into the zone comprising the active ingredients, damaging or altering the properties of the active ingredients, as well as migration of the active ingredients into the surrounding components is also highly undesired as the active ingredient will spread beyond the target area. In some cases the active ingredients may be aggressive to the surroundings, e.g. in the case of acids, and may attack and damage the other parts of the dressing.

A way of decreasing these problems is to introduce a barrier layer separating the active ingredient from the adhesive. The barrier layer may be in the form of a polymer or metal layer impermeable to the active ingredient and to the surrounding dressing materials such as the adhesive.

In U.S. Pat. No. 4,711,781 is disclosed a drug delivery device comprising a plurality of separate medicated zones on a carrier, the medicated composition being separated from the carrier layer by a barrier layer. The barrier layer is in the form of flat circular pieces under the medication dots. Cup-shaped barriers are also known in the art.

However, even when using these barrier layers/cups, migration is still a problem. It is difficult, seen from a production point of view, to handle the border line between the barrier layer and the surroundings. The adhesive as well as the medication tends to migrate anyway. Furthermore, many medical adhesives tend to cold-flow during storage or use.

GB Patent Application No. 2 184 016 discloses a transdermal device for administration of medicaments. The device has a cup-shaped barrier layer enclosing the active agent, the rim of the cup extending into a flange. The problem of migration during storage is solved by sealing the flange to the release liner. However, the sealing process adds another step to the production process as well as the strength of the seal may be difficult to control, causing a risk that the active agent may follow the release liner instead of the device when separated before use.

Thus there is still a need for a medicated patch where the migration of the medication is minimized.

It has surprisingly been shown that by providing the barrier layer separating a first and a second layer with a flange on which flange the second component only is present in a thin coating the migration is reduced to an acceptable level.

BRIEF DESCRIPTION OF THE INVENTION

The invention relates to an article having an adhesive surface for adhering to human skin, said article comprising a first component constituting a continues layer and at least a second component which is located in indentations in the adhesive surface of the first component, said second component being separated from the first component by a cup shaped barrier layer, said barrier layer being provided with a rim extending into a flange.

The invention further relates to method of topical treatment of the skin or a wound.

BRIEF DESCRIPTION OF THE DRAWING

The invention is explained more in detail with reference to the drawing in which.

DETAILED DESCRIPTION OF THE INVENTION

Figure 1:
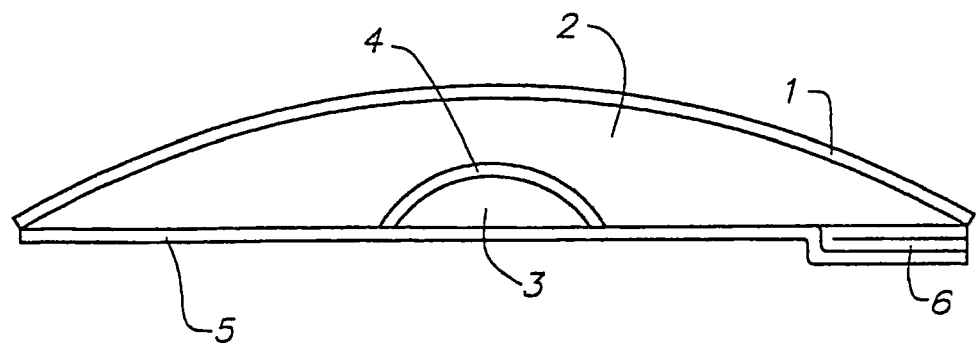
FIG. 1 shows a cross-section of an article representing the state of the art.

The present invention relates to an article having an adhesive surface for adhering to human skin, said article comprising a first component constituting a continuous layer and at least a second component which is located in indentations in the adhesive surface of the first component. The second component is separated from the first component by a cup shaped barrier layer, said barrier layer being provided with a rim extending into a flange wherein the second component is present on the flange in a layer having an average thickness of less than 0.045 mm.

In a preferred embodiment of the invention the second component may be present on the flange in a layer having an average thickness of less than 0.040 mm.

In a more preferred embodiment of the invention the second component may be present on the flange in a layer having an average thickness of less than 0.030 mm.

A method of producing an article with two or more separate components, may be to introduce the second component into the first component in such a way that the skin facing surface of the dressing will comprise zones of both components and will be substantially planar. The skin facing surface may, until use, optionally comprise a protection layer, such as a release liner. The second component may be in the form of one or more dots or separate zones, located in indentations in the first component. At the skin-facing surface of the article the first and the second component will only be in contact with each others by the rim of the coated flange. By controlling the thickness of the second layer on the flange, the contact zone between the two components will be reduced to a level where the migration is at an acceptable level.

It has surprisingly been shown that when the second component is present on the flange in a layer having a thickness of less than 0.045 mm, the migration of the second component is negligible.

The flange may extend from the rim of the cup and inwards or it may extend outwards from the centre of the second component.

By using the inward flange a smaller contact zone to the skin than the size of the component is achieved. In this way an article with an increased amount of the second composition together with a limited skin-contacting zone is achieved. The second component may thus act as a reservoir.

When the flange is outwards all of the skin facing surface of the second component is in contact with the skin, while a part of the first component is covered by the flange. The flange is coated with a thin layer of the second component which may be an advantage as the skin-contacting zone of this component thus is enlarged. In the case where the second component comprises an active ingredient, a central zone with a high level of active ingredient surrounded by the zone of the flange with a lower level of active ingredient is achieved.

In one embodiment of the invention the flange faces both inward and outward from the edge of the cup.

The barrier layer may be of any suitable material being impermeable to the components of the dressing. Preferred materials may be polymer films, metal foils, such as aluminium or a laminate of one or more layers of suitable materials.

In one embodiment of the invention the barrier layer comprises a polymer film.

In another embodiment of the invention the barrier layer comprises a metal foil.

In a preferred embodiment of the invention the barrier layer comprises a laminate of one or more layers of polymer films and/or metal foils.

The barrier layer may comprise polymer films or laminates of such, coated with a metal layer.

The first component may be any suitable material for such articles, such as adhesives, absorbent material or foams.

The first component may comprise an adhesive. The adhesive may be in the form of a coating on the skin facing surface of the component.

The first component of the dressing may preferably be an adhesive. The adhesive may be any skin friendly adhesive. The adhesive may contain hydrocolloids.

The adhesive of an article of the invention may be any skin-friendly adhesive known per se being able to adhere to the skin, the mucosa and/or a wound on any portion of a living being and is preferably an adhesive comprising a hydrocolloid. A suitable adhesive is e.g. a hydrocolloid-containing moisture absorbing material such as the adhesive disclosed in U.S. Pat. No. 4,367,732. The adhesive may also comprise a skin friendly acrylate adhesive containing hydrophilic areas. The adhesive may be essentially uniform or be constituted by distinct areas having different composition such as the adhesives disclosed in WO89/05619 or in WO94/15562.

Suitable hydrocolloids for incorporation in the adhesive compositions of the invention are selected from naturally occurring hydrocolloids, semi-synthetic hydrocolloids and synthetic hydrocolloids.

Few substances can be applied on the skin as they are. In order to avoid an irritant effect or solubility problems, it is often advantageous to mix or dissolve the active ingredients in a suitable vehicle.

The second component of the dressing may be a releasing vehicle such as foam, alginate, gel, petrolatum or an adhesive, preferably a hydrocolloide containing adhesive. The releasing vehicle may be polymeric material capable of controlled release of the active ingredient.

In a preferred embodiment of the invention the second component may comprise one or more active ingredients, such as pharmaceutically or biologically active ingredients.

The second component of the article of the invention may comprise wound healing associated indicator(s) such as indicators of pH, partial pressure of $O_2$, temperature, radical mechanisms or biotechnological assays, e.g. indicating formation of collagen.

It is also advantageous that an article according to the invention comprises wound healing associated indicator(s), cushions or similar device for treatment or prophylaxis of formation of wounds and/or skin abnormalities.

This opens for a combined medical treatment of a wound or skin and an easy and sterile application of the active ingredients, e.g. by incorporating active ingredients such as a cytokine such as growth hormone or a polypeptide growth factor giving rise to the incorporation of such active substances in a form being apt to local application in a wound in which the medicament may exercise its effect on the wound, other medicaments such as bacteriostatic or bactericidal compounds, e.g. iodine, iodopovidone complexes, chloramine, chlorohexidine, silver salts such as sulphadiazine, silver nitrate, silver acetate, silver lactate, silver sulphate, silver-sodium-thiosulphate or silver chloride, zinc or salts thereof, metronidazol, sulpha drugs, and penicillins, tissue-healing enhancing agents, e.g. RGD tripeptides and the like, proteins, amino acids such as taurine, vitamins such as ascorbic acid, D-vitamine derivatives, enzymes for cleansing of wounds, e.g. pepsin, trypsin and the like, proteinase inhibitors or metalloproteinase inhibitors such as Illostat or ethylene diamine tetraacetic acid, cytotoxic agents and proliferation inhibitors for use in for example surgical insertion of the product in cancer tissue and/or other therapeutic agents which optionally may be used for topical application, antioxidants, antihistamines, fungicides, nicotine, nitroglycerine, antiinflamatory drugs, NSAIDS, cortico steroids, pain relieving agents such as lidocaine, benzocaine or chinchocaine, emollients, retinoids or agents having a cooling effect, as well as herbal agents or medicine, which is also considered an aspect of the invention.

In one embodiment of the invention the active component is suitable for treating corns, warts or callous skin.

In an especially preferred embodiment of the invention the second component comprises an active ingredient suitable for the treatment of corns, warts and callous skin.

A suitable component may be an acid such as lactic or salicylic acid.

It is especially preferred that the active ingredient is salicylic acid. The salicylic acid may be incorporated in a vehicle such as an adhesive.

The article according to the invention may be especially suitable for use for controlled topical administration of one or more active ingredients.

The article may be a wound dressing or a dermal or transdermal patch.

The article according to the invention may comprise one cup-shaped barrier layer.

The article of the invention may comprise a plurality of cup-shaped barrier layers. The cups may be arranged in a pattern over the dressing in order to distribute the active ingredients to the skin or wound in a desired way.

For use as topical application of an active ingredient to the skin or a wound, the skin contacting zone of the second component may be designed to correspond in size to the lesion, and the article will protect the lesion while in use, is preferably waterproof, and can easily be peeled off and discarded.

An article according to the invention is typically in the form of a laminate comprising a backing layer, a layer of adhesive and which optionally is covered in part or fully by one or more release liners or cover films to be removed before use. The device may further comprise a secondary backing layer to be removed before use.

The backing layer of the article according to the invention may be any layer, such as a polyurethane film, foam or non-wowen or combination of films or layers which, in combination with the adhesive, shows the desired characteristics of the article according to the invention. The film may e.g. be produced from a polyolefinic material, PVAl, polyester, polyamid, polyurethane material or polyethylene or copolymers or blends thereof.

The film may be biodegradable or solubilised under certain conditions.

A preferred material for the backing layer may be polyurethane in the form of a film or a foam or combinations of such e.g. in the form of laminates.

The skin-contacting surface of the device may be covered by one or more release liners.

Release liners which are especially suitable for use with the device of the invention can be made of kraft papers, polyethylene, polypropylene, polyester or composites of any of these materials. The liners are preferably coated with release agents such as fluorochemicals or silicones. The release liner may, if present, be removed before, during, or after application. If only removed after application, the release liner may act as a handle during application.

Even though the invention is described with two components it is understood that more than two components may be included and such embodiments are thus a part of the present invention.

The invention further relates to a method for topical treatment of a wound or skin site by placing an article having an adhesive surface for adhering to human skin. The article includes a first component constituting a continuous layer and at least a second component which is located in indentations in the adhesive surface of the first component. The second component is separated from the first component by a cup shaped barrier layer, with the barrier layer being provided with a rim extending into a flange wherein the second component is present on the flange in a layer having an average thickness of less than 0.045 mm on the skin or wound site to be treated, with the skin-contacting surface of the second component located over the site to be treated.

The second component, optionally comprising one or more active ingredients, may then donate the active ingredients to the skin site to be treated, while the surrounding healthy skin is protected from the influence of the second component by the first component.

DETAILED DESCRIPTION OF THE DRAWING

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

FIG. 1 shows cross-section of a dressing of the state of the art, comprising a carrier layer (1), a first component, such as an adhesive layer (2), a second component (3), such as a medicated zone and a cup shaped barrier layer (4) separating the two components. The skin contacting surface of the article is covered with release-liners (5,6). It can be seen that the rim of the barrier layer (4) is narrow and thus easy to enter.

This barrier layer, optionally a film or foil, provides only a thin barrier between the components, and even the slightest inaccuracy in the production of the article may result in direct contact between the two components. Even when the barrier layer is correctly placed, one or more of the components may be able to migrate under the edge of the barrier.

Figure 2:
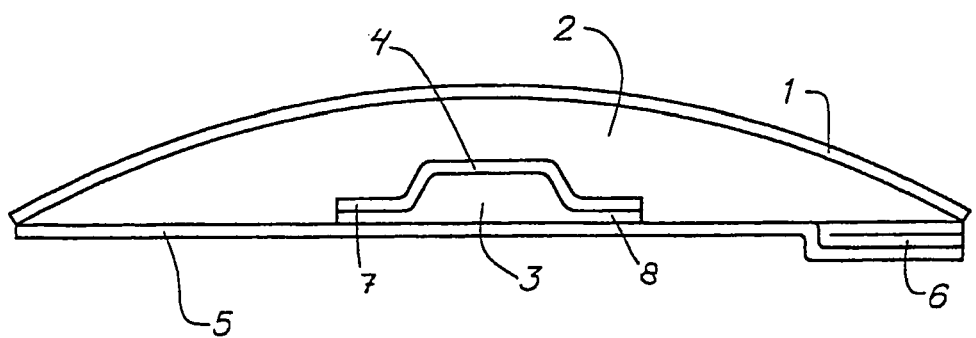
FIG. 2 shows a cross-section of an article according to the invention.

FIG. 2 shows a cross-section of an embodiment of the invention comprising a carrier layer (1), a first component (2), a second component (3), and a barrier layer (4) separating the two components. The skin contacting surface or the article is covered with release-liners (5,6). The rim of the barrier layer (4) is elongated into a flange (7) stretching outwards from the centre of the article. The flange (7) is coated with a layer (8) of the second component.

By separating the first and the second component by a cup-shaped barrier layer, the cup being provided with a rim extending into a flange at the skin-facing surface of the article, a broader distance between the main portions of the two components is achieved, and the level of migration is decreased. The migration taking place may only arise from the edge portion of the second component being coated on the flange, and by reducing the thickness of this layer the migration is minimized.

Figure 3:
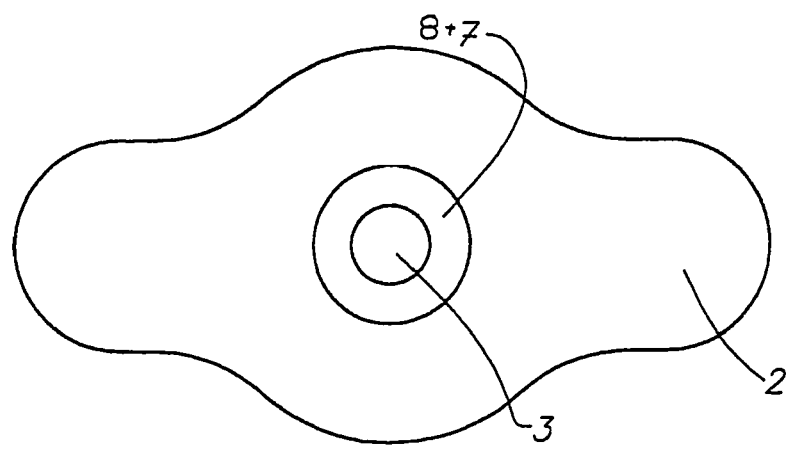
FIG. 3 shows an article according to the invention seen from below.

FIG. 3 shows the embodiment of the invention of FIG. 2 seen from below, comprising the first component (2) surrounding the second component (3), separated by the barrier layer with the flange (7) covered with the second component (8).

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. An article having an adhesive surface for adhering human skin, said article comprising:
    a first component comprising a continuous layer and an adhesive disposed on the continuous layer;
    a barrier layer comprising a first side that is coupled to the adhesive of the first component and a second side opposite the first side, said second side of said barrier layer forming a cup shaped portion defined by a rim extending into a flange; and
    a second component including an active ingredient, the second component disposed inside the cup shaped portion and outside of the cup shaped portion on said second side of said barrier layer from said rim to a perimeter of said flange.

2. The article according to claim 1, wherein the second component disposed on said second side of said barrier layer from said rim to said perimeter of said flange has an average thickness of less than 0.045 mm.

3. The article according to claim 1, wherein the barrier layer includes a polymer film.

4. The article according to claim 1, wherein that the barrier layer includes a metal foil.

5. The article according to claim 1, wherein the barrier layer includes a laminate of one or more layers of polymer films and/or metal foils.

6. The article according to claim 1, wherein the second component includes an adhesive.

7. The article according to claim 1, wherein the article is a wound dressing.

8. The article according to claim 1, wherein the article is a transdermal patch.

9. The article according to claim 1, wherein the active ingredient is suitable for treating corns, warts or callous skin.

10. The article according to claim 1, wherein the active ingredient is salicylic acid.

11. The article according to claim 1, wherein the active ingredient of the second component is a topical medicament.

12. The article of claim 2, wherein the second component is deposited over substantially all of the second side of the barrier layer.

13. The article of claim 2, wherein the active ingredient in the second component migrates into the adhesive of the first component only through the thickness of the second component at said perimeter of said flange that is in contact with said adhesive of the first component.

14. The article of claim 1, wherein the adhesive of the first component extends to a perimeter of the article, and the second component disposed from said rim to said perimeter of said flange is co-planar with the adhesive of the first component at the perimeter of the article.

15. The adhesive article of claim 14, further comprising:
a release liner disposed over the article in contact with the first and second components.

16. An adhesive article comprising:
a first component comprising a continuous layer and an adhesive disposed on the continuous layer;
a barrier layer comprising a first side that is coupled to the adhesive of the first component and a second side opposite the first side, the second side of the barrier layer forming a cup shaped portion defined by a rim and a flange extending from the rim to a perimeter of the barrier layer; and
a second component including an active ingredient, the second component disposed in the cup shaped portion and over the flange to the perimeter of the barrier layer.

17. The adhesive article of claim 16, wherein the adhesive of the first component extends to a perimeter of the adhesive article, and the second component disposed over the flange is co-planar with the adhesive of the first component at the perimeter of the adhesive article.

18. The adhesive article of claim 16, wherein the second component disposed over the flange has an average thickness of less than 0.045 mm.

19. The adhesive article of claim 16, wherein the second component including the active ingredient is in contact with the adhesive of the first component only through a thickness of the second component as measured at the perimeter of the barrier layer.

20. An adhesive article comprising:
a first component comprising a continuous layer and an adhesive disposed on the continuous layer;
a barrier layer comprising a first side that is coupled to the adhesive of the first component and a second side opposite the first side, the second side of the barrier layer forming a cup shaped portion defined by a rim and a flange extending from the rim to a perimeter of the barrier layer; and
a second component including an active ingredient, the second component disposed in the cup shaped portion and over the flange to the perimeter of the barrier layer;
wherein the second component disposed over the flange has an average thickness of less than 0.045 mm and is so configured to reduce migration of the active ingredient into the adhesive of the first component.

21. The adhesive article of claim 20, wherein the second component including the active ingredient is in contact with the adhesive of the first component only through a thickness of the second component as measured at the perimeter of the barrier layer.

* * * * *